United States Patent
Sirch et al.

(10) Patent No.: US 7,462,747 B2
(45) Date of Patent: Dec. 9, 2008

(54) PROCESS FOR PREPARING POLYALCOHOLS FROM FORMALDEHYDE HAVING A LOW FORMIC ACID CONTENT

(75) Inventors: Timan Sirch, Schifferstadt (DE); Michael Steiniger, Neustadt (DE); Steffen Maas, Bubenheim (DE); Stefan Rittinger, Mannheim (DE); Stephan Schlitter, Limburgerhof (DE); Maria Guixa, Mannheim (DE); Todd C. Spengeman, Missouri City, TX (US); Jeffrey T. Andress, Lake Jackson, TX (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/797,007

(22) Filed: Apr. 30, 2007

(65) Prior Publication Data

US 2008/0167506 A1    Jul. 10, 2008

(30) Foreign Application Priority Data

Jan. 5, 2007    (EP)    ................................... 07100160

(51) Int. Cl.
  *C07C 37/20*    (2006.01)
  *C07C 27/04*    (2006.01)
  *C07C 29/14*    (2006.01)
(52) U.S. Cl. ........................ 568/799; 568/862; 568/891
(58) Field of Classification Search ........................ None
  See application file for complete search history.

(56) References Cited

U.S. PATENT DOCUMENTS

| | | | |
|---|---|---|---|
| 3,808,280 | A | 4/1974 | Merger et al. |
| 4,122,290 | A | 10/1978 | Immel et al. |
| 4,288,640 | A | 9/1981 | Schuster et al. |
| 4,386,018 | A | 5/1983 | Merger et al. |
| 6,018,074 | A * | 1/2000 | Kratz et al. ................. 560/234 |
| 6,187,971 | B1 | 2/2001 | Kratz et al. |
| 6,201,160 | B1 | 3/2001 | Brudermuller et al. |
| 6,448,457 | B1 | 9/2002 | Hesse et al. |

FOREIGN PATENT DOCUMENTS

| | | |
|---|---|---|
| DE | 941-633 | 4/1956 |
| DE | 1957 591 | 5/1971 |
| DE | 2040 501 | 2/1972 |
| DE | 27 02 582 | 7/1978 |
| DE | 0 044 444 | 1/1982 |
| DE | 196 53 093 A 1 | 6/1998 |
| GB | 1 362 071 | 7/1974 |
| WO | WO 95/32171 | 11/1995 |
| WO | WO 98/28253 A1 | 7/1998 |
| WO | WO 99/44974 | 9/1999 |
| WO | WO 01/47853 A1 | 7/2001 |

* cited by examiner

*Primary Examiner*—Sikarl A Witherspoon
(74) *Attorney, Agent, or Firm*—Oblon, Spivak, McClelland, Maier & Neustadt, P.C.

(57) ABSTRACT

The invention relates to a process for preparing polymethylol compounds of the formula (I)

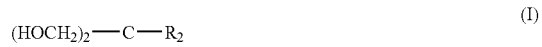

where the radicals R are each, independently of one another, a further methylol group or an alkyl group having from 1 to 22 carbon atoms or an aryl or aralkyl group having from 6 to 22 carbon atoms, by condensation of aldehydes having from 2 to 24 carbon atoms with formaldehyde in an aldol reaction using tertiary amines as catalyst to form alkanals of the formula (II)

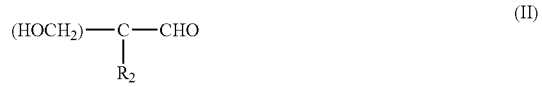

where the radicals R each independently have one of the abovementioned meanings, and subsequent hydrogenation of the latter. The particular inventive feature of this process is that the aldol reaction is carried out using an aqueous formaldehyde solution having a formic acid content of <150 ppm and preferably <100 ppm.

In this way of carrying out the process, the formation of by-products can advantageously be prevented in a targeted manner and the yield of the desired polymethylol compound can thereby be increased.

20 Claims, No Drawings

PROCESS FOR PREPARING POLYALCOHOLS FROM FORMALDEHYDE HAVING A LOW FORMIC ACID CONTENT

The invention relates to a process for preparing polymethylol compounds, generally also referred to as polyalcohols, such as neopentyl glycol or trimethylolpropane.

Among the polyalcohols mentioned, neopentyl glycol ("NPG") and trimethyolpropane ("TMP"), for example, are used in the plastics sector for the production of surface coatings, urethanes and polyesters. They are usually prepared industrially by the Cannizzaro process. To prepare trimethylolpropane by this process, n-butyraldehyde is reacted with an excess of formaldehyde in the presence of an inorganic base. One equivalent of an inorganic formate is formed at the same time as coproduct. The separation of the salt from trimethylolpropane is complicated and incurs additional expense. Furthermore, the inorganic salt has to be worked up and purified if it is to be utilized in a beneficial way and the formation of the coproduct represents a loss of the stoichiometric amounts of sodium hydroxide and formaldehyde used. In addition, the yields based on n-butyaldehyde in this inorganic Cannizzaro reaction are unsatisfactory since high-boiling constituents which cannot be utilized further are formed during the course of the reaction.

Similar problems as indicated for trimethylolpropane are present in the preparation of other polyalcohols such as trimethylolethane (from n-propanal and formaldehyde) or trimethylolbutane (from n-pentanal and formaldehyde) or neopentyl glycol (from isobutyraldehyde and formaldehyde). To avoid these disadvantages, WO 98/28253 has disclosed a process for preparing polyalcohols in which aldehydes having from 2 to 24 carbon atoms are firstly condensed with formaldehyde in an aldol reaction using tertiary amines as catalysts to form the corresponding alkanals and these are subsequently hydrogenated to the corresponding polyalcohols (hydrogenation process). This process is low in coproduct. After the first stage, unreacted aldehydes and part of the amine base are generally separated off from the methylolalkanal by distillation and recirculated. The distillation bottoms comprise the products of the aldolization, viz. the methylolalkanals, for example hydroxypivalaldehyde ("HPA"), together with water, the formic acid salts of the base used and formic acid itself. In this process, the methylolalkanal is obtained as a 20-70% strength by weight aqueous solution.

If polyhydric alcohols such as pentaerythritol, neopentyl glycol ("NPG") or trimethylolpropane ("TMP") are to be prepared from aqueous methylolalkanal solutions, these solutions have to be hydrogenated.

This hydrogenation is generally carried out at temperatures above 80° C. Redissociations of the methylol group to the free aldehyde and also ether, ester and acetal formation are observed in the hydrogenation reactor. These secondary reactions lead to low hydrogenation selectivities and to low yields of polyhydric alcohol.

In addition, many hydrogenation catalysts are not stable under these conditions. In particular, catalysts based on the oxides of copper, as are known from EP-A 44 444 and DE-A 19 57 591, continuously lose hydrogenation activity in the presence of these aqueous methylolalkanal solutions under hydrogenation conditions, their operating life decreases and in the worst case they become unusable.

It has been recognized that formic acid, which is present in the formaldehyde as a result of its method of production or has been formed as by-product from formaldehyde by means of a Cannizzaro reaction during the aldol reaction, is decomposed into $CO_2$ and $H_2$ or into CO and $H_2O$ during the course of the hydrogenation. CO and $CO_2$ can be detected in the offgas from the hydrogenation. It has now been observed that the decomposition rate of the formic acid is dependent on the temperature and on the age of the catalyst.

CO and $CO_2$ have been found to be catalyst poisons which have an adverse effect on the hydrogenation activity, in particular of copper catalysts. The deliberate addition of CO or $CO_2$ to the hydrogen led to a significant decrease in the hydrogenation activity of the copper catalyst even when the $H_2$ partial pressure, the absolute amount of $H_2$ and the pH in the hydrogenation reactor were kept constant.

The reduced hydrogenation activity of the catalyst can be compensated over at least part of the time by increasing the reaction temperature. However, a disadvantage is that secondary reactions increase with rising reaction temperatures and result in not only increased usages but also contaminated product. Thus, for example, a retroaldol reaction takes place as the temperature increases in the hydrogenation of hydroxypivalaldehyde or of dimethylolbutanal to the corresponding alcohols NPG and TMP. The aldehydes formed here are hydrogenated to undesirable by-products (in the case of NPG, isobutanol and methanol are formed in this way and in the case of TMP 2-methylbutanol, 2-ethyl-1,3-propanediol and methanol are formed) and the yield is reduced correspondingly. In the case of the synthesis of NPG, increased formation of the cyclic acetal of NPG and HPA is observed at elevated temperature. This by-product cannot be separated from NPG by distillation and therefore leads to a less pure desired product. Furthermore, high temperatures promote the thermal Tishchenko reaction of HPA to form the neopentyl glycol ester of hydroxypivalinic acid (HPN). Owing to these secondary reactions, increasing the temperature as a means of keeping the hydrogenation activity of a catalyst constant is limited by economic factors such as yield and product purity.

It was therefore an object of the invention to provide a process for preparing polymethylol compounds by condensation of aldehydes with formaldehyde in an aldol reaction using tertiary amines as catalyst to form the corresponding alkanals and their subsequent hydrogenation, as has become known from, for example, WO 98/28253, which is hereby expressly incorporated by reference, in which the redissociation of methylol alkanals which have been formed is largely suppressed, the formation of ethers, esters and acetals is largely prevented and a positive effect is exerted on the operating life of the catalyst. In addition, the process should make it possible to obtain polyhydric alcohols with good hydrogenation selectivities and yields.

This object is achieved by a process in which the desired polymethylol compounds of the formula (I)

where the radicals R are each, independently of one another, a further methylol group or an alkyl group having from 1 to 22 carbon atoms or an aryl or aralkyl group having from 6 to 22 carbon atoms, are prepared by condensation of aldehydes having from 2 to 24 carbon atoms with formaldehyde in an aldol reaction using tertiary amines as catalyst to form alkanals of the formula (II)

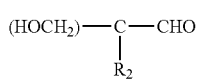

$$(HOCH_2)-\underset{R_2}{C}-CHO \quad (II)$$

where the radicals R each independently have one of the abovementioned meanings, and are subsequently hydrogenated, wherein the aldol reaction is carried out using an aqueous formaldehyde solution having a formic acid content of less than 150 ppm, preferably <100 ppm, preferably <50 ppm.

Industrially available formaldehyde is usually marketed in aqueous solution in concentrations of 30, 37 and 49% by weight. This technical-grade formaldehyde comprises formic acid as a result of its production by dehydrogenation of methanol. This formic acid content increases further during storage of technical-grade formaldehyde. It has been found that the use of an aqueous formaldehyde solution having a formic acid content which is greatly reduced according to the invention enables long operating lives of the hydrogenation catalysts together with a good yield to be achieved.

Preference is given to using a formaldehyde or an aqueous formaldehyde solution which has been treated with commercial basic ion exchangers. Possible anion exchangers are strong base, weak base and medium base gel or macroporous ion exchangers known per se. These are, for example, anion exchangers having a polystyrene structure crosslinked with divinylbenzene and bearing tertiary amino groups as functional groups. Ionic exchangers based on acrylic acid or methacrylic acid crosslinked with divinylbenzene or resins prepared by condensation of formaldehyde and phenol are also possibilities.

Specific examples of possible anion exchangers are the commercial products Ambersep® 900, Amberlyst® and Amberlite® from Rohm and Haas, Philadelphia, USA, and also Lewatit® from Lanxess, Leverkusen.

In carrying out the process of the invention, which will be described by way of example for the preparation of neopentyl glycol without being restricted thereto, isobutyraldehyde is firstly reacted with an aqueous solution of formaldehyde having a formic acid content of less than 150 ppm, preferably <100 ppm, preferably <50 ppm, and a catalyst in the form of a tertiary amine in an aldol reaction. This gives a mixture of hydroxypivalaldehyde, unreacted isobutyraldehyde and formaldehyde and also the amine catalyst mentioned and possibly water.

The reaction mixture mentioned is subsequently fed into a distillation apparatus in which it is separated into readily volatile and less volatile constituents. The distillation conditions are selected so that a low boiler fraction comprising unreacted isobutyraldehyde, formaldehyde, possibly water and part of the amine catalyst as significant components is formed. This low boiler fraction is used again in carrying out the aldol reaction, as described above.

After the low boiler fraction has been separated off, a relatively nonvolatile bottom product consisting essentially of hydroxypivalaldehyde and water and also part of the amine catalyst remains in the indicated work-up by distillation.

Due to the reduced formic acid content according to the invention of the aqueous formaldehyde solution, pronounced by-product formation of ethers and acetals need not be feared.

The hydroxypivalaldehyde obtained in this way is then catalytically hydrogenated by means of hydrogen in a manner known per se to form neopentyl glycol.

As an alternative to the mode of operation described above, the process of the invention can also be carried out with the reaction mixture obtained in the aldol reaction being fed into a phase separator instead of a distillation apparatus and a separation of the reaction mixture into an aqueous phase and an organic phase occurring in this phase separator. It is here possible to use the phase separation apparatuses customarily used for liquid-liquid separations, as are described in Ullmanns Encyklopädie der technischen Chemie, 4th edition, volume 2, pp. 560-565, Verlag Chemie, Weinheim, 1972.

The aldol reaction is generally carried out at a temperature of from 5 to 100° C., preferably from 15 to 80° C., and the residence time is generally set to from 0.25 to 12 hours, depending on the temperature.

In the aldol reaction, the molar ratio of freshly added isobutyraldehyde to the amount of formaldehyde added is advantageously from 1:2 to 1:5, preferably from 1:2 to 1:3.5. The amount of tertiary amine catalyst added in the aldol reaction is, based on the isobutyraldehyde added, generally from 0.001 to 0.2 equivalent, preferably from 0.01 to 0.07 equivalent, i.e. the amine is used in catalytic amounts.

The subsequent distillation to separate the reaction mixture into a low boiler fraction and the bottom product is generally carried out at from 50 to 200° C., preferably from 90 to 160° C., and a pressure of generally from 0.1 mbar to 10 bar, preferably from 0.5 to 5 bar, in particular atmospheric pressure.

This gives an aldolization product which consists essentially of methylolalkanal such as hydroxypivalaldehyde or, depending on the starting compounds used, the corresponding alkanal. This serves as hydrogenation feed and is catalytically hydrogenated in a suitable hydrogenation reactor.

Catalysts which can be used according to the invention are catalysts which are suitable for hydrogenations and preferably comprise at least one metal of transition groups 8 to 12 of the Periodic Table of the Elements, e.g. Fe, Ru, Os, Co, Rh, Ir, Ni, Pd, Pt, Cu, Ag, An, Zn, Cd, Hg, preferably Fe, Co, Ni, Cu, Ru, Pd, Pt, particularly preferably Cu, preferably on a customary support material, particularly preferably on one of the oxides of titanium, zirconium, hafnium, silicon and/or aluminum. The catalysts which can be used according to the invention can be produced by methods known from the prior art for producing such supported catalysts. Preference is also given to using supported catalysts comprising copper on a support material comprising aluminum oxide or titanium dioxide in the presence or absence of one or more of the elements magnesium, barium zinc and chromium. Such catalysts and their production are known from WO 99/44974.

Furthermore, copper-comprising supported catalysts as are described, for example, in WO 95/32171 and the catalysts disclosed in EP-A 44 444 and DE 19 57 591 are also suitable for the hydrogenation according to the invention.

The hydrogenation can be carried out batchwise or continuously, e.g. in a reactor tube filled with a catalyst bed, with the reaction solution being passed over the catalyst bed, e.g. in the downflow or upflow mode, as described in DE-A 19 41 633 or DE-A 20 40 501. It can be advantageous to recirculate a substream of the output from the reaction, if appropriate with cooling, and pass it over the fixed catalyst bed again. Likewise, it can be advantageous to carry out the hydrogenation in a plurality of reactors connected in series, for example in from 2 to 4 reactors, with the hydrogenation reaction being carried out only to a partial conversion of, for example, from 50 to 98% in the individual reactors upstream of the last reactor and the hydrogenation being completed only in the last reactor. It can here be advantageous to cool the hydrogenation output from the preceding reactor before it enters the next reactor, for example by means of cooling devices or by injection of cold gases such as hydrogen or nitrogen or introduction of a substream of cold reaction solution.

The hydrogenation temperature is generally in the range from 50 to 180° C., preferably from 90 to 140° C. The hydrogenation pressure employed is generally from 10 to 250 bar, preferably from 20 to 120 bar.

The hydrogenation feed is mixed with tertiary amine upstream of the inlet into the hydrogenation reactor until the hydrogenation output has a pH of from 7 to 9. It is also possible to feed the hydrogenation feed of the tertiary amine separately into the reactor and mix them there.

Otherwise, it is possible to employ any hydrogenation methods and use hydrogenation catalysts as are customary for the hydrogenation of aldehydes and are described in detail in the standard literature.

The crude neopentyl glycol obtained in this way can be purified by distillation in a customary manner.

The process of the invention can be carried out with or without addition of organic solvents or solubilizers. The addition of solvents or solubilizers can prove to be advantageous, especially when long-chain aldehydes are used as starting materials. The use of solvents which form suitable minimum boiling point anisotropic mixtures with the low-boiling compounds in the individual distillations of the process of the invention may enable the energy consumption in these distillations to be reduced and/or the separation of the low boilers from the high-boiling compounds by distillation to be made easier.

Suitable solvents are, for example, cyclic and acyclic ethers such as THF, dioxane, methyl tert-butyl ether or alcohols such as methanol, ethanol or 2-ethylhexanol.

The reaction procedures described for the aldolization reaction can be carried out at a pressure of generally from 1 to 30 bar, preferably from 1 to 15 bar, particularly preferably from 1 to 5 bar, advantageously under the autogenous pressure of the reaction system concerned.

The novel process can be applied to virtually all alkanals having a methylene group in the α position relative to the carbonyl group. It is possible to use aliphatic aldehydes which have from 2 to 24 carbon atoms and can be linear or branched or comprise alicyclic groups as starting materials. It is likewise possible to use araliphatic aldehydes as starting materials, provided that they comprise a methylene group in the α position relative to the carbonyl group. In general, use is made of aralkyl aldehydes having from 8 to 24 carbon atoms, preferably from 8 to 12 carbon atoms, for example phenylacetaldehyde, as starting materials. Preference is given to aliphatic aldehydes having from 2 to 12 carbon atoms, for example 3-ethylbutanal, 3-n-propylbutanal, 3-isopropylbutanal, 3-n-butylbutanal, 3-isobutylbutanal, 3-sec-butylbutanal, 3-tert-butylbutanal and also corresponding -n-pentanals, -n-hexanals, -n-heptanals, 4-ethylpentanal, 4-n-propylpentanal, 4-isopropylpentanal, 4-n-butylpentanal, 4-isobutylpentanal, 4-sec-butylpentanal, 4-tert-butylpentanal, corresponding -n-hexanals, -n-heptanals; 5-ethyl-n-hexanal, 5-n-propyl-n-hexanal, 5-isopropyl-n-hexanal, 5-n-butyl-n-hexanal, 5-isobutyl-n-hexanal, 5-sec-butyl-n-hexanal, 5-tert-butyl-n-hexanal, corresponding -n-heptanals; 3-methylhexanal, 3-methylheptanal; 4-methylpentanal, 4-methylheptanal, 5-methyl-hexanal, 5-methylheptanal; 3,3,5-trimethyl-n-pentyl, 3,3-diethylpentyl, 4,4-diethylpentyl, 3,3-dimethyl-n-butyl, 3,3-dimethyl-n-pentyl, 5,5-dimethylheptyl, 3,3-dimethylheptyl, 3,3,4-trimethylheptyl, 3,4-dimethylheptyl, 3,3-dimethylheptyl, 4,4-dimethylheptyl, 3,3-diethylhexyl, 4,4-dimethylhexyl, 4,5-dimethylhexyl, 3,4-dimethylhexyl, 3,5-dimethylhexyl, 3,3-dimethylhexyl, 3,4-diethylhexyl, 3-methyl-4-ethylpentyl, 3-methyl-4-ethylhexyl, 3,3,4-trimethylpentyl, 3,4,4-trimethylpentyl, 3,3,4-trimethylhexyl, 3,4,4-trimethylhexyl, 3,3,4,4-tetramethylpentyl aldehyde; in particular $C_2$-$C_{12}$-n-alkanals.

Apart from the abovementioned neopentyl glycol whose preparation has been described here in terms of its essentials and by way of example, preference is also given to using n-butyraldehyde for preparing trimethylolpropane, acetaldehyde for preparing pentaerythritol, propionaldehyde for preparing trimethylolethane and n-pentanal for preparing trimethylolbutane.

Tertiary amines which are suitable for the condensation of aldehydes with formaldehyde are amines known per se, as described, for example, in DE-A 28 13 201 and DE-A 27 02 582. Particular preference is given to tri-n-alkylamines such as triethylamine, tri-n-propylamine, tri-n-butylamine and in particular trimethylamine.

The process of the invention gives high yields, based both on the starting aldehyde and on the formaldehyde, and leads to very small losses of amine catalyst. The invention is illustrated below with the aid of examples.

EXAMPLES

Determination of the Formic Acid Content

The formic acid content of the formaldehyde in ppm (parts per million) was determined acidimetrically using an aqueous solution of NaOH (0.01 mol/L). The determination was carried out using a Metrohm TiNet titration system with Titrino 736GP with Dosimat E685, a Metrohm combined glass electrode (6.0210.100) and a Metrohm temperature sensor PT100/PT1000.

46 g of formaldehyde in the form of a 49% strength aqueous solution was diluted to 100 ml with HPLC water at room temperature. The sample was titrated dynamically with NaOH solution to the end point (EP1) at pH 6-6.5.

The formic acid content was calculated according to:

$$\frac{\text{Consumption } (EP1) \text{ in ml } (NaOH) \times 460}{\text{weight in g}} = ppm \text{ of } HCOOH$$

Hydrogenation of Hydroxypivalaldehyde to Neopentyl Glycol

Comparative Example

Hydrogenation Feed A a) Aldolization 1,1 mol of isobutyraldehyde were stirred with 1 mol of formaldehyde in the form of a 49% strength by weight solution having a content of 1.5% by weight of methanol and 200 ppm of formic acid and 4 mol % of trimethylamine, based on isobutyraldehyde, at 75° C. for 1 h. The reaction solution was concentrated by distilling off low boilers such as isobutyraldehyde and part of the water at atmospheric pressure. The bottoms obtained comprised 75% by weight of hydroxypivalaldehyde, 20% by weight of water and about 5% by weight of other organic secondary components.

Example 1

Hydrogenation Feed B

An aqueous formaldehyde solution having a content of 49% by weight of formaldehyde, 1.5% by weight of methanol and 200 ppm of formic acid was passed over the commercial, basic ion exchanger Ambersep® 900 OH from Rohm and Haas Company, Philadelphia, USA. After this treatment, the formic acid content was determined by means of titration and found to be 10 ppm.

Hydrogenation of Hydrogenation Feeds A and B a) Catalyst Activation 150 ml of a $Cu/Al_2O_3$ catalyst as described in example 1 of EP 44444 were activated at 190° C. in a tube reactor by passing a mixture of 5% by volume of hydrogen and 95% by volume of nitrogen (total volume: 50 standard l/h) over the catalyst at atmospheric pressure for 24 hours.

Hydrogenation

The mixture described above as hydrogenation feed A served as starting solution. The hydrogenation feed is passed downward at an $H_2$ pressure of 37 bar through the reactor heated to 105° C. The WHSV was 0.2 kg of hydroxypivalaldehyde/($I_{cat.}$*h). A pH of 7.9 in the hydrogenation output was set by addition of trimethylamine in the form of a 15% strength by weight solution to the hydrogenation feed. Part of the hydrogenation output is mixed back into the feed (recycle mode). A mean conversion of 95.3% at a mean pH of 8.8 was achieved over a number of days.

The feed was subsequently changed over to the hydrogenation feed B according to the invention. The mean conversion at this setting was 95.9%.

The invention claimed is:

1. A process for preparing polymethylol compounds of formula (I)

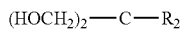  (I)

comprising:
condensing an aldehyde having from 2 to 24 carbon atoms with formaldehyde in an aldol reaction to form an alkanal of formula (II);

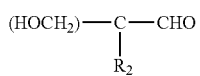  (II)

and
hydrogenating the alkanal of formula (II); wherein
the radicals R are each, independently of one another, a further methylol group or an alkyl group having from 1 to 22 carbon atoms or an aryl or aralkyl group having from 6 to 22 carbon atoms,
the condensing an aldehyde with formaldehyde is catalyzed by a tertiary amine, and
the formaldehyde is an aqueous formaldehyde solution having a formic acid content of <150 ppm.

2. The process according to claim 1, wherein the formic acid content of the aqueous formaldehyde solution is <100 ppm.

3. The process according to claim 1, wherein the alkanal of formula (II) is one selected from the group consisting of propionaldehyde, n-butyraldehyde, acetaldehyde and isobutyraldehyde and the prepared polymethylol compound of formula (I) is correspondingly trimethylolethane, trimethylolpropane, pentaerythritol or neopentyl glycol.

4. The process according to claim 1, wherein the condensing and hydrogenating are carried out continuously.

5. The process according to claim 1, wherein the tertiary amine catalyst is present in such an amount that a pH of from 5 to 12 is established.

6. The process according to claim 1, wherein the tertiary amine is trimethylamine.

7. The process according to claim 1, wherein a molar ratio of alkanal to formaldehyde is in the range 1:2 to 1:5.

8. The process according to claim 7, wherein the molar ratio of alkanal to formaldehyde is in the range 1:2 to 1:3.5.

9. The process according to claim 1, wherein 0.001 to 0.2 equivalents of tertiary amine, based on alkanal, are present in the condensing of an alkanal with formaldehyde.

10. The process according to claim 9, wherein 0.01 to 0.07 equivalents of tertiary amine, based on alkanal, are present in the condensing of an alkanal with formaldehyde.

11. The process according to claim 1, further comprising treating the formaldehyde with a basic ion exchanger prior to use in the condensing of an alkanal with formaldehyde.

12. The process according to claim 2, wherein the formic acid content of the aqueous formaldehyde solution is <50 ppm.

13. The process according to claim 1, further comprising distilling a reaction mixture obtained by the condensing of an alkanal with formaldehyde, wherein
a low boiling fraction comprising unreacted alkanal and formaldehyde is recycled to the condensing of an alkanal with formaldehyde.

14. The process according to claim 1, wherein a solvent or solubilizer is added.

15. The process according to claim 14, wherein the solvent or solubilizer is at least one selected from the group consisting of tetrahydrofuran, dioxane, methyl tert-butyl ether, methanol, ethanol and 2-ethylhexanol.

16. The process according to claim 1, wherein a temperature of the condensing of an alkanal with formaldehyde is in the range from 5 to 100° C.

17. The process according to claim 16, wherein the temperature of the condensing of an alkanal with formaldehyde is in the range from 15 to 80° C.

18. The process according to claim 1, wherein a temperature of the hydrogenating is in the range from 50 to 180° C.

19. The process according to claim 18, wherein the temperature of the hydrogenating is in the range from 90 to 140° C.

20. The process according to claim 1, wherein a pressure of the hydrogenating is in the range from 10 to 250 bar.

* * * * *